(12) United States Patent
Syed et al.

(10) Patent No.: US 10,213,187 B1
(45) Date of Patent: Feb. 26, 2019

(54) METHOD AND APPARATUS FOR PERCUTANEOUS SUPERFICIAL TEMPORAL ARTERY ACCESS FOR CAROTID ARTERY STENTING

(71) Applicants: Mubin Syed, Springfield, OH (US); Al Stancampiano, Waban, MA (US); Ashfaq Ahmed, Springfield, OH (US)

(72) Inventors: Mubin Syed, Springfield, OH (US); Al Stancampiano, Waban, MA (US); Ashfaq Ahmed, Springfield, OH (US)

(73) Assignee: Mubin I. Syed, Springfield, OH (US)

( * ) Notice: Subject to any disclaimer, the term of this patent is extended or adjusted under 35 U.S.C. 154(b) by 198 days.

(21) Appl. No.: 13/750,920

(22) Filed: Jan. 25, 2013

Related U.S. Application Data

(60) Provisional application No. 61/590,472, filed on Jan. 25, 2012.

(51) Int. Cl.
*A61B 8/08* (2006.01)

(52) U.S. Cl.
CPC ..................... *A61B 8/48* (2013.01)

(58) Field of Classification Search
CPC ......................................... A61B 8/48
USPC ................................. 600/437–469
See application file for complete search history.

(56) References Cited

U.S. PATENT DOCUMENTS

| 4,243,040 A | 1/1981 | Beecher |
| 5,098,707 A | 3/1992 | Baldwin et al. |
| 5,293,772 A | 3/1994 | Carr, Jr. |
| 5,344,426 A | 9/1994 | Lau et al. |
| 5,419,777 A | 5/1995 | Hofling |
| 5,571,135 A | 11/1996 | Fraser et al. |
| 5,651,366 A * | 7/1997 | Liang .................. A61B 8/12 600/439 |
| 5,662,703 A | 9/1997 | Yurek et al. |

(Continued)

FOREIGN PATENT DOCUMENTS

| CN | 108472124 A | 8/2018 |
| CN | 108472472 A | 8/2018 |

(Continued)

OTHER PUBLICATIONS

Stroke Treatments; American heart association. Http://www.strokeassociation.org/STROKEORG/AboutStroke/Treatment/Stroke-Treatments_UCM_310892_Article.jsp#V9Hrg2WfV_1.

(Continued)

*Primary Examiner* — Sanjay Cattungal
(74) *Attorney, Agent, or Firm* — Jennifer Hayes; Nixon Peabody LLP

(57) ABSTRACT

An ultrasound imaging system provides coronal and transverse images for guiding a superior temporal artery guidewire (STA guidewire) through a tortuous region of the STA to an aortic arch region for snaring by a femoral artery catheter snare and pulling through for "through and through" guidewire access. The STA guidewire includes a knob at a distal end which is advanced into a superficial temporal artery (STA) using multi-plane ultrasound guidance, and the STA guidewire is guided through the tortuous region using transverse and coronal images provided by the multi-plane ultrasound imager. The transverse and coronal images indicate the rotational direction for the wire tip to advance the knob end of the STA guidewire within the STA to the external carotid artery.

13 Claims, 10 Drawing Sheets

(56) References Cited

U.S. PATENT DOCUMENTS

| | | |
|---|---|---|
| 5,669,924 A | 9/1997 | Shaknovich |
| 5,690,644 A | 11/1997 | Yurek et al. |
| 5,718,702 A | 2/1998 | Edwards |
| 5,720,735 A | 2/1998 | Dorros |
| 5,807,330 A | 9/1998 | Teitelbaum |
| 5,957,901 A | 9/1999 | Mottola et al. |
| 6,027,462 A | 2/2000 | Greene et al. |
| 6,059,813 A | 5/2000 | Vrba et al. |
| 6,070,589 A | 6/2000 | Keith et al. |
| 6,152,141 A | 11/2000 | Stevens et al. |
| 6,238,410 B1 | 5/2001 | Vrba et al. |
| 6,245,017 B1 | 6/2001 | Hashimoto |
| 6,450,964 B1 | 9/2002 | Webler |
| 6,663,613 B1 | 12/2003 | Lewis et al. |
| 6,780,174 B2 | 8/2004 | Mauch |
| 6,808,520 B1 | 10/2004 | Fouirkas et al. |
| 6,837,881 B1 | 1/2005 | Barbut |
| 6,929,633 B2 | 8/2005 | Evans et al. |
| 6,942,682 B2 | 9/2005 | Vrba et al. |
| 7,235,083 B1 | 6/2007 | Perez et al. |
| 7,758,624 B2 | 7/2010 | Dorn et al. |
| 7,763,010 B2 | 7/2010 | Evans et al. |
| 7,766,961 B2 | 8/2010 | Patel et al. |
| 7,842,026 B2 | 11/2010 | Cahill et al. |
| 8,092,509 B2 | 1/2012 | Dorn et al. |
| 8,241,241 B2 | 8/2012 | Evans et al. |
| 8,343,181 B2 | 1/2013 | Duffy et al. |
| 8,535,290 B2 | 9/2013 | Evans et al. |
| 8,727,988 B2 | 5/2014 | Flaherty et al. |
| 8,740,971 B2 | 6/2014 | Iannelli |
| 8,986,241 B2 | 3/2015 | Evans et al. |
| 8,998,894 B2 | 4/2015 | Mauch et al. |
| 9,314,499 B2 | 4/2016 | Wang et al. |
| 9,636,244 B2 | 5/2017 | Syed |
| 9,980,838 B2 | 5/2018 | Syed |
| 2001/0003985 A1* | 6/2001 | Lafontaine .................. A61F 2/06 128/898 |
| 2001/0049534 A1 | 12/2001 | Lachat |
| 2002/0077691 A1 | 6/2002 | Nachtigall |
| 2002/0123698 A1 | 9/2002 | Garibotto et al. |
| 2002/0156518 A1 | 10/2002 | Tehrani |
| 2002/0165535 A1 | 11/2002 | Lesh |
| 2003/0088187 A1* | 5/2003 | Saadat .................... A61B 5/015 600/547 |
| 2003/0216721 A1 | 11/2003 | Diederich |
| 2003/0229282 A1 | 12/2003 | Burdette |
| 2004/0073190 A1 | 4/2004 | Deem et al. |
| 2004/0138734 A1 | 7/2004 | Chobotov et al. |
| 2004/0147837 A1* | 7/2004 | Macaulay ............... A61B 34/20 600/424 |
| 2005/0043779 A1 | 2/2005 | Wilson |
| 2005/0101968 A1 | 5/2005 | Dadourian |
| 2005/0113862 A1 | 5/2005 | Besselink et al. |
| 2005/0222488 A1 | 10/2005 | Chang et al. |
| 2006/0025752 A1 | 2/2006 | Broaddus et al. |
| 2006/0025844 A1 | 2/2006 | Majercak et al. |
| 2006/0030923 A1 | 2/2006 | Gunderson |
| 2006/0155363 A1 | 7/2006 | LaDuca et al. |
| 2006/0200221 A1 | 9/2006 | Malewicz |
| 2006/0257389 A1 | 11/2006 | Binford |
| 2006/0259063 A1 | 11/2006 | Bates et al. |
| 2006/0270900 A1* | 11/2006 | Chin .................. A61B 1/00096 600/104 |
| 2007/0016019 A1 | 1/2007 | Salgo |
| 2007/0016062 A1 | 1/2007 | Park |
| 2007/0038061 A1* | 2/2007 | Huennekens .......... A61B 6/504 600/407 |
| 2007/0038293 A1 | 2/2007 | St. Goar et al. |
| 2007/0049867 A1 | 3/2007 | Shindelman |
| 2007/0083215 A1 | 4/2007 | Hamer et al. |
| 2007/0118151 A1 | 5/2007 | Davidson et al. |
| 2007/0129719 A1* | 6/2007 | Kendale ............. A61B 1/00096 606/41 |
| 2008/0039746 A1* | 2/2008 | Hissong ............. A61B 19/5244 601/3 |
| 2008/0114239 A1 | 5/2008 | Randall et al. |
| 2008/0194993 A1 | 8/2008 | McLaren et al. |
| 2008/0208309 A1 | 8/2008 | Saeed |
| 2009/0005679 A1 | 1/2009 | Dala-Krishna |
| 2009/0036780 A1 | 2/2009 | Abraham |
| 2009/0132019 A1 | 5/2009 | Duffy et al. |
| 2009/0171293 A1 | 7/2009 | Yang et al. |
| 2009/0177035 A1* | 7/2009 | Chin .................. A61B 1/00165 600/112 |
| 2009/0240253 A1 | 9/2009 | Murray |
| 2009/0254116 A1 | 10/2009 | Rosenschein et al. |
| 2009/0270975 A1 | 10/2009 | Gifford, III et al. |
| 2009/0319017 A1* | 12/2009 | Berez ..................... A61F 2/844 623/1.3 |
| 2010/0016943 A1 | 1/2010 | Chobotov |
| 2010/0024818 A1 | 2/2010 | Stenzler et al. |
| 2010/0030165 A1* | 2/2010 | Takagi ................. A61L 29/085 604/265 |
| 2010/0030256 A1* | 2/2010 | Dubrul ............... A61B 10/0266 606/200 |
| 2010/0069852 A1 | 3/2010 | Kelley |
| 2010/0168583 A1* | 7/2010 | Dausch ..................... A61B 8/12 600/466 |
| 2010/0185161 A1* | 7/2010 | Pellegrino .......... A61B 17/3472 604/272 |
| 2010/0185231 A1 | 7/2010 | Lashinski |
| 2010/0204708 A1 | 8/2010 | Sharma |
| 2010/0268067 A1* | 10/2010 | Razzaque ............. A61B 8/4245 600/424 |
| 2010/0272740 A1 | 10/2010 | Vertegel et al. |
| 2011/0009943 A1 | 1/2011 | Paul et al. |
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0020942 A1 | 1/2012 | Hall et al. |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1* | 2/2012 | Whiting ............. A61B 17/3468 604/528 |
| 2012/0169712 A1 | 7/2012 | Hill et al. |
| 2012/0209375 A1 | 8/2012 | Madrid et al. |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0296773 A1 | 11/2013 | Feng et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0142427 A1 | 5/2014 | Petroff |
| 2014/0214002 A1 | 7/2014 | Thermopeutix |
| 2014/0228808 A1 | 8/2014 | Webster et al. |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0245933 A1 | 9/2015 | Syed |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Van Bladel et al. |
| 2017/0119562 A1 | 5/2017 | Syed |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |

(56) References Cited

U.S. PATENT DOCUMENTS

| | | |
|---|---|---|
| 2018/0042743 A1 | 2/2018 | Syed |
| 2018/0059124 A1 | 3/2018 | Syed |
| 2018/0250147 A1 | 9/2018 | Syed |

FOREIGN PATENT DOCUMENTS

| | | |
|---|---|---|
| EP | 8280355 A1 | 2/2018 |
| EP | 3367969 A1 | 9/2018 |
| EP | 3368123 A1 | 9/2018 |
| WO | WO1996/036269 | 11/1996 |
| WO | 2011/011539 A1 | 1/2011 |
| WO | WO2011/106502 | 9/2011 |
| WO | 2010/129193 A1 | 11/2011 |
| WO | 2011/137336 A1 | 11/2011 |
| WO | WO2012/030101 | 8/2012 |
| WO | 2014081947 | 5/2014 |
| WO | WO2014/197839 | 12/2014 |
| WO | 2016164215 | 10/2016 |
| WO | 2017/074492 A1 | 5/2017 |
| WO | 2017/074536 A1 | 5/2017 |
| WO | 2017/127127 A1 | 7/2017 |
| WO | 2017222571 A1 | 12/2017 |
| WO | 2017222612 A1 | 12/2017 |

OTHER PUBLICATIONS

Beckman, Michele G. et al., "Venous thromboembolism: a public health concern"; Am J Prev Med. Apr. 2010;38(4 Suppl): S495-501.

Meunier, Jason M., et al., ""Individual Lytic Efficacy of Recombinant Tissue Plasminogen Activator in an in-vitro Human Clot Model: Rate of "Nonresponse" Acad Emerg Med. May 2013; 20(5): 449-455.

Tripathi, Ramesh C., et al. "Use of Tissue Plasminogen Activator for Rapoid Dissolution of Fibrin and Blood Clots in the Eye After Surgery for Claucomoa and Cataract in Humans" Drug Development Research; vol. 27, Issue 2, pp. 147-159, 1992.

Office Action issued in U.S. Appl. No. 14/683,010 dated Sep. 27, 2016.

International Search Report / Written Opinion issued in Int'l Application No. PCT/US2016/024794 dated Jul. 1, 2016, 10 pages.

International Search Report / Written Opinion issued in Inn Application No. PCT/US2016/047163 dated Oct. 28, 2016, 9 pages.

International Search Report / Written Opinion issued in Int'l Application No. PCT/US2016/024795 dated Aug. 30, 2016, 14 pages.

International Search Report and Written Opinion issued for International Application No. PCT/US2016/047165 dated Jan. 5, 2017, 13 pages.

International Preliminary Report on Patentability issued in International Application No. PCT/US2016/024795 dated May 1, 2018, 10 pages.

International Preliminary Report on Patentability issued in International Application No. PCT/US2016/047165 dated May 1, 2018, 5 pages.

Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.

International Search Report and Written Opinion issued for International Application No. PCT/US2017/021188 dated May 10, 2017, 11 pages.

International Search Report and Written Opinion issued for PCT/US2018/012834 dated Mar. 15, 2018,13 pages.

Godwin, J., The Circulatory and Respiratory Systems, Z0250 Lab III, 2002, retrieved from: https://projects.ncsu.edu/cals/course/zo250/lab-3.html.

International Search Report issued in Int'l Application No. PCT/US2013/071271 dated Feb. 10, 2014, 2 pages.

International Preliminary Report on Patentability issued in International Application No. PCT/US2013/071271 dated May 26, 2015, 6 pages.

Written Opinion issued in International Application No. PCT/US2013/071271 dated Feb. 10, 2014, 5 pages.

* cited by examiner

Arterial Vascular Overview

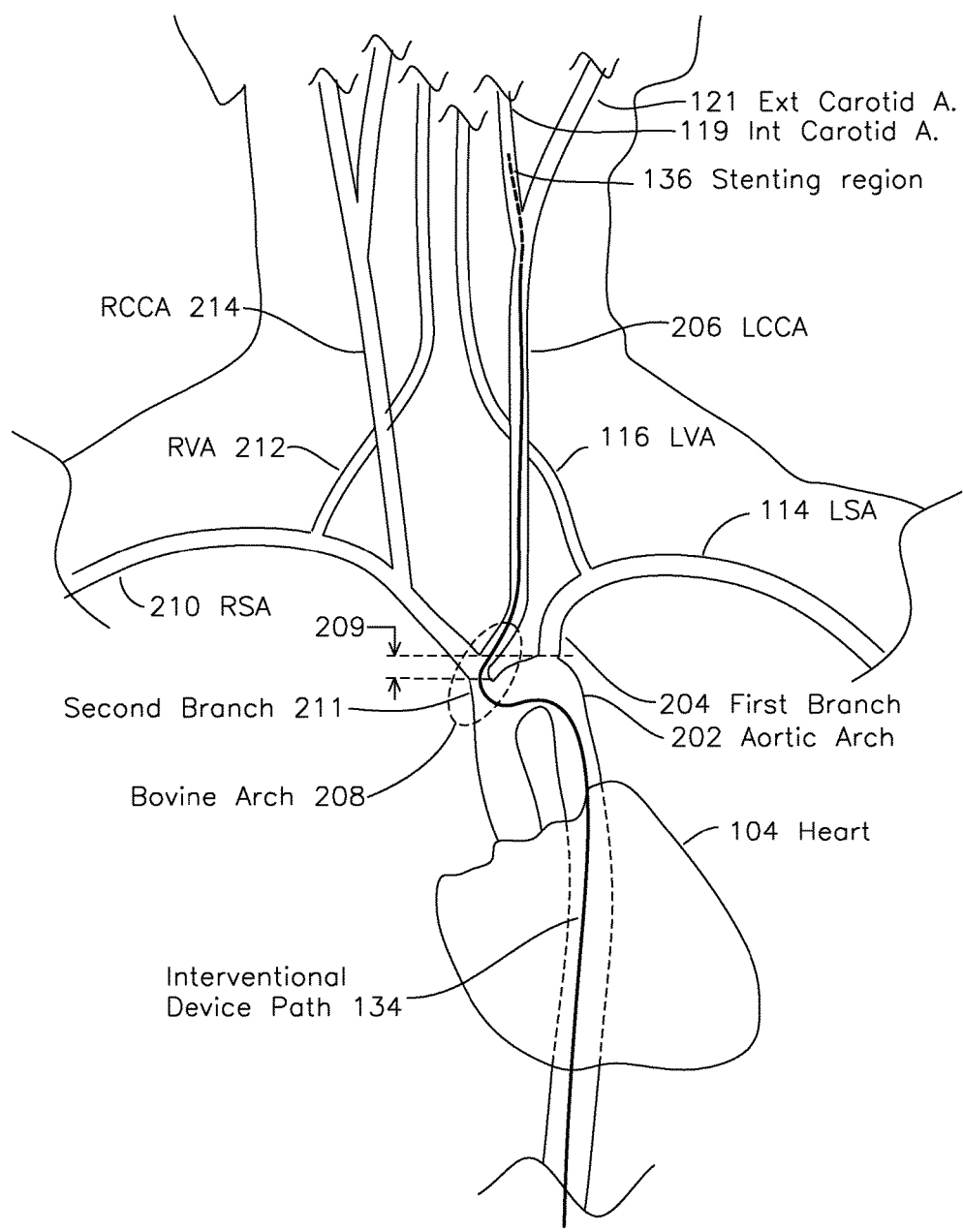

Type IIa Bovine Aortic Arch Access:

Type IIa Bovine Aortic Arch Access:

Type III Aortic Arch Access

Superficial Temporal Artery access

Tri-plane ultrasound transducer

Bi-plane ultrasound transducer

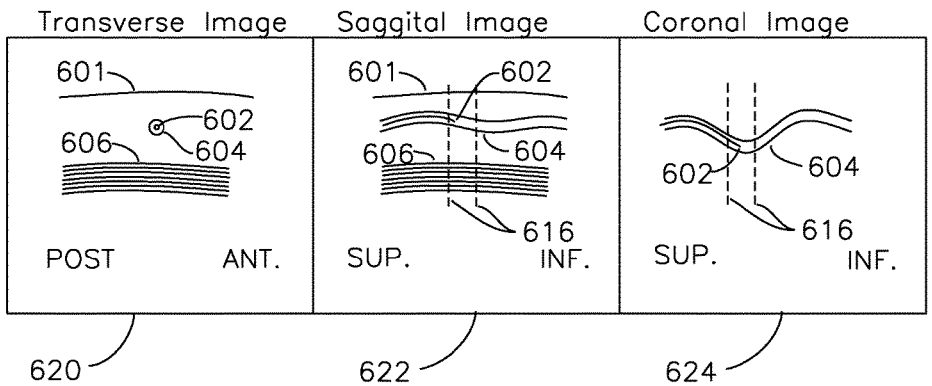
Figure 6
Image Display – STA guidewire
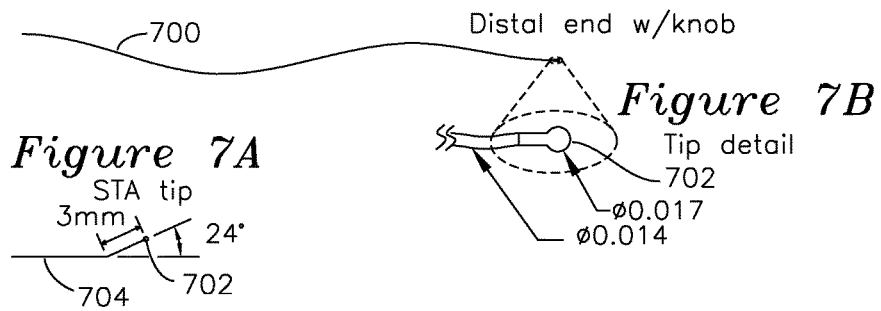
Figure 7
STA guidewire (first guidewire)
Figure 7A
STA tip
Figure 7B
Tip detail
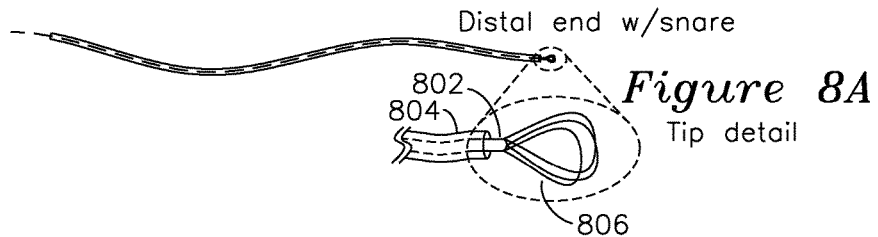
Figure 8
FA Catheter (second guidewire w/snare in catheter)
Figure 8A
Tip detail Superficial Temporal Artery access Transverse Plane ultrasound imaging of STA Quasi-Coronal Plane ultrasound imaging of STA Image Display – guided needle entry Image Display – STA guidewire entry

METHOD AND APPARATUS FOR PERCUTANEOUS SUPERFICIAL TEMPORAL ARTERY ACCESS FOR CAROTID ARTERY STENTING

The present patent application claims priority to provisional patent application 61/590,472 filed Jan. 25, 2012.

FIELD OF THE INVENTION

The present invention relates to an imaging device which enables the placement of a guidewire which is prerequisite for the installation of a stent in the carotid artery of a patient with a hostile aortic arch. In particular, the invention relates to the use of multi-plane ultrasound imaging to allow the introduction of a guidewire into the Superficial Temporal Artery (STA), the STA guidewire being subsequently snared by a guidewire introduced into the femoral artery and guided to the aortic arch or carotid artery.

BACKGROUND OF THE INVENTION

FIG. 1 shows a subset of the arterial vascular system of a subject 102 in need of a stent, and for clarity in understanding the issues related to guiding the stent into a human patient, the venous system, organs, pulmonary arteries and veins, and many branches of the circulatory system are not shown. Heart 104 pumps oxygenated blood through the aortic arch 106, which guides upward-flowing blood from the heart to a downward flow for delivery to the lower organs and right femoral artery 120 and left femoral artery 122, which are interchangeably used for stent arterial access, as will be described later. Many variations in the vessels formed in a subject are found from one subject to another, and the particular subject 102 shown in FIG. 1 has an aortic arch 106 with three major branching vessels which leave the aortic arch, including a first branching vessel which forms the left subclavian artery (LSA) 114 and left vertebral artery (LVA) 116, a second branching vessel which forms the left common carotid artery 118 (LCCA), and a third branching vessel which forms the right subclavian artery (RSA) 108, right vertebral artery (RVA) 110, and right common carotid artery (RCCA) 112.

Arteriosclerotic disease processes known as Atherosclerosis often afflict the arterial system, and the affected areas include the aortic arch 106, left common carotid artery 118 (branching to internal carotid artery 119 and external carotid artery 121), and right common carotid artery 112 (which also branch to internal and external carotid arteries, not shown). The disease processes which take place in these vessels cause deterioration of the interior vessel walls, and diseased material which detaches from the interior vessels can be swept through the arterial system with successively decreasing vessel diameter until it becomes lodged in a vessel constriction, causing the cessation of blood flow in the blocked area, leading to tissue death from loss of oxygenation. This disease process is the leading cause of strokes, heart attacks, and other debilitating or fatal events. When a subject presents with this disease process, a variety of imaging techniques may be used to ascertain the nature of the blockage or potential blockage, using contrast agents and x-ray or magnetic resonance (MR) imaging, including computerized axial tomography (CAT) scans, whereby the imaging contrast agent provides increased differentiation between the vessel walls and the blood flowing through the vessel.

As atherosclerosis in the carotid artery progresses, the risk of stroke increases, and it becomes necessary to intervene to prevent stroke or death from clots or vessel debris which becomes lodged in the brain, specifically related to disease of the internal carotid artery branch which serves the brain, or the common carotid artery which precedes it in the circulatory path. It should be noted that stroke is the third leading cause of death in the developed nations. 85% of all strokes are ischemic (due to brain circulation compromise) in nature and 20-30% of all ischemic strokes are caused by carotid artery atherosclerotic occlusive disease. For atherosclerotic occlusive disease of the internal or common carotid artery, one procedure performed by interventionalists (interventional radiologists, vascular surgeons, or interventional cardiologists) is the installation of a stent, which is an expanding cylindrical wire or plastic mesh which supports and stabilizes the diseased area of the artery, and reduces the stenosis (narrowing) of the artery through a treatment known as angioplasty, whereby an inflatable balloon is used to momentarily expand the stent across the inner diameter of the vessel in the stenotic region.

The prior art installation of a carotid artery stent described for FIG. 1 is done in a series of steps for which the order of the steps and types of equipment may vary. As will be described, the types of interventional devices which are used in the procedures include a small diameter guidewire which may be co-inserted with a small catheter, a subsequently inserted stiff guidewire which may be co-inserted or replace the small diameter guidewire in the small catheter, a sleeve or sheath which may be threaded over the small catheter, and an angioplasty catheter which may be threaded over the small catheter or exchanged for the small catheter during the procedure. For clarity, FIG. 1 broadly indicates the path 135 used by interventional devices in the example (where the interventional devices may represent any of the previously described devices in any combination and achieving an insertion level which is typically less than the entire path length 135, which extends to the ultimate treatment region 136 reached by the stent catheter.

Following FIG. 1, the first step of a stenting procedure involves threading the small diameter guidewire, which may be a 0.035 inch diameter steerable guidewire having a bent tip, where the tip may also be hydrophilic) through a steerable catheter which may also have a bent tip for steering. Examples of such steerable catheter guidewires are Berenstein or Vertebral with trade names H1H or Headhunter) or reverse curve (Simmons or Vitek). Steering is done by rotating the guidewire, which causes the bent tip to select the desired artery and follow that arterial path with the catheter following and assisting in selection. The first step therefore is the installation at percutaneous location 132 of a femoral artery (FA) catheter, which is usually 4 to 6 French diameter, and guided into the femoral artery through the aortic arch 106 and to the common carotid artery 118. The guidewire is fed from a sterile drape 130 which furnishes the approximately 260 cm of length required. The external carotid artery (ECA) 121 is then selected often with the angled FA catheter and same guidewire followed by selection of an external carotid artery branch while the guidewire is advanced.

Navigational information on the progress of the guidewire is provided by a radiographic display which is used in combination with arterial contrast agents which delineate the vessel walls with respect to the guidewire. One typical imaging system is x-ray fluoroscopy, whereby a source of x-rays is applied in one or more planes through the patient to a 2D or 3D detector, and the real-time radiographic images are used by the interventionalist to provide guidance information. The small diameter guidewire inside the catheter is then replaced with a stiff guidewire (to eventually support the subsequently placed long guiding sleeve or sheath). The small diameter catheter may or may not be removed at this point leaving the stiff guidewire in place. The long guiding sleeve or sheath (6 to 8 French) is then advanced over the stiff guidewire alone (or over the catheter and stiff guidewire combination) from the femoral access through the descending aorta region 134 and through the aortic arch region 106 to the distal common carotid artery 118 just below the bifurcation. Contrast injection is performed through the guiding sleeve or sheath to now visualize the internal carotid artery 119 and external carotid artery 121. The stiff guidewire in the ECA 121 is typically removed at this point. The stenosis in the internal carotid artery (ICA) 119 is gently traversed with a 0.014 inch guidewire tip fixed embolic protection device (EPD), examples of which are manufactured under the trade names Accunet or Filterwire, versus a embolic protection device that is separately deployed over a 0.014 inch guidewire with a 0.017 inch tip, such as those with trade names Nav6 or Emboshield. The EPD is deployed within the distal portion of the cervical segment of the ICA 119. An angioplasty balloon catheter is then threaded through the sheath over the guidewire portion of the EPD to the location of the stenosis 136 to then predilate the stenosis. The angioplasty catheter is then exchanged for a stent delivery catheter which has a self expanding stent at the distal end, which is guided to the site of the stenosis 136 shown in FIG. 1. A slightly larger angioplasty balloon catheter is then used to postdilate the stent to the desired diameter. Carotid and cerebral angiography is then perform to confirm an adequate result.

The critical part of steering occurs when selecting the particular vessel of the aortic arch shown in FIG. 1. Each subject 102 undergoing the procedure may have a different aortic arch vascular configuration. FIG. 1 shows a common arrangement of vessels at the aortic arch, as was previously described, and the radiographic contrast agent is injected to delineate the vessel outlines, which enables the interventionalist to select and steer into the vessel which leads to the desired carotid artery, shown as the left internal carotid artery 119 with the expanding stent on the distal end of the stent delivery catheter, which was introduced after the angioplasty catheter as previously described. The stent may be a wire or plastic mesh which is guided into place and affixed by inflating a balloon which deforms the stent to conform to the inner diameter of the blood vessel. Many variations in the arrangement of arteries which branch from the aortic arch may be present, and are classified according to "type" where the type number signifies the extent of vertical deviation (or slope) of the bifurcation point for arteries which branch at the top of the aortic arch. FIG. 1 shows three arteries which branch from the top of the aortic arch 106 in substantially the same horizontal plane, and is known as a "type 1" aortic arch. A "type 2" aortic arch has one of the branching arteries located 1-2 common carotid artery diameters below the topmost, and a "type 3" aortic arch has a separation from horizontal of more than 2 common carotid artery diameters. Since the stent delivery catheter is advanced from the descending aorta region 134 to the top of the aortic arch 106, the type number provides an indication of how difficult the navigation to the common carotid artery will be according to the extent to which the catheter must change direction to guide into the common carotid artery, as will be described. As can be seen from FIG. 1, the long guiding sleeve or sheath can be guided into the left common carotid artery 118 without significant changes in direction along the path. The long guiding sleeve or sheath is typically placed in the common carotid artery 118 just below the bifurcation point for the external carotid artery 121 and internal carotid artery 119, after which the angioplasty catheter and stent delivery catheter are guided into the desired artery such as the internal carotid artery 119 as shown in FIG. 1.

FIG. 2A shows a magnified view of an aortic arch region 202 variation from 106 of FIG. 1, where the subject of FIG. 2A has a type II aortic arch variation (branching artery 211 is 1-2 carotid artery diameters below the first branch 204 indicated by distance 209) in vascular configuration and also a branch point for the LCCA 206 above second branch 211, known collectively as a type II-A Bovine aortic arch 208, which is distinguishable from FIG. 1 having three branches at the top of the aortic arch. The type II-A Bovine aortic arch has only two branches 204 and 211 at the top of the aortic arch, with the left common carotid artery 206 not having its own vessel leading to the aortic arch (as was the case in FIG. 1), but instead branching off from second branch 211 which also forms the right common carotid artery 214, right vertebral artery 212, and right subclavian artery 210. One difficulty that can be seen from the LCCA 206 geometry of FIG. 2A is that the initial guidewire entry into the LCCA from the aortic arch 202 is a sharp turn in a vessel transitioning from the large diameter aortic arch 202 to the much smaller diameter LCCA 206, and additionally with a sharp angle of approach and difficult catheter guidance. This type of Bovine aortic arch can be difficult to navigate without insult or injury to the adjacent inner walls of the aorta, which are likely to also have atherosclerosis as the region to be treated by angioplasty, and this agitation during guidance may cause diseased vessel material to break loose and cause a stroke during the installation of the stent—which original purpose was to reduce such risk. Blood vessels which present these risks associated with atherosclerosis and with difficult entry geometry are known as hostile vessels, and accordingly, the aortic arch of FIG. 2A is known as a hostile aortic arch, with the aortic arch type classification indicating the level of difficulty and type of difficulty for FA catheter guidance to the carotid artery.

It is desired to provide an apparatus and method for installation of a carotid artery stent which eases the navigation of the guidewire through hostile vessels of the aortic arch, thereby reducing patient risk and procedure length, and accordingly increasing patient safety.

It is also desired to provide an apparatus and method for through-and-through access and guidance through tortuous vessels by using a major vessel for entry of a catheter into a large vessel in combination with the entry of a guidewire into a minor surface vessel, the apparatus and method for use with or without a multi-plane imaging device for navigating the tortuous vessel region.

OBJECTS OF THE INVENTION

A first object of the invention is an apparatus for the installation of a stent, the apparatus also providing a method for guiding a therapeutic instrument to a desired location, the apparatus including an imaging device for the insertion and guidance of a Superficial Temporal Artery (STA) guidewire with a snare attachment on the distal end to a snaring region for engagement with an FA catheter having a snare on a distal end of the FA catheter, the imaging device performing multi-plane imaging of the STA guidewire during subcutaneous entry and initial guidance through tortuous vessels.

A second object of the invention is a process for imaging a region to enable guiding an STA guidewire which has a snare attachment on a distal end, the process having: an FA guidewire and catheter installation step whereby the FA guidewire and catheter are inserted into the femoral artery of a subject and advanced to within a navigation distance of an aortic arch;

an STA guidewire installation step whereby an STA guidewire is guided into a vessel having a tortuous surface region or tortuous path using a multi-plane image provided by an ultrasonic transducer having multiple imaging planes, at least one image plane having an angle between 30 and 90 degrees with respect to an imaging surface, and at least one image plane which is perpendicular to the image surface and also perpendicular to the first image plane;

an engagement step whereby the STA guidewire distal end and FA catheter distal end are coupled to each other;

a through and through step, whereby either the FA catheter or the STA guidewire are withdrawn beyond the location of engagement, thereby providing a single guidewire or catheter for subsequent use.

SUMMARY OF THE INVENTION

A multi-plane imaging device generates multiple planar views of the Superficial Temporal Artery (STA) and allows guidance of an STA guidewire as it enters the STA, the STA guidewire (first guidewire) having a distal knob (also known as a distal head) forming an attachment for coupling to a snare provided by a femoral artery (FA) catheter and guidewire inserted into a femoral artery of a subject. The multi-plane imaging device displays simultaneous multiple planar views indicating the relationship between an STA guidewire needle introducing the STA guidewire into a vessel, and the STA guidewire with respect to the STA, thereby allowing guidance of the wire into this vessel, which has many sharp turns near the skin surface. A vessel with the property of many sharp turns is known as a tortuous vessel, and presents difficulty in STA guidewire needle introduction and STA guidewire steering, as the combination of the small guidewire and tortuosity of the vessel increases the likelihood of an undesired exit puncture of the tortuous vessel, either by the STA guidewire needle, or the STA guidewire itself. Once successfully introduced, the STA guidewire may be advanced through the vessel to a snaring region such as the aortic arch of the subject. A second guidewire and catheter, referenced herein as the "FA catheter" is guided into the snaring region using the guidewire for steering. The guidewire is subsequently withdrawn from the central lumen of the catheter and a snare is fed into the catheter lumen, the snare having distal snaring loops for gripping the STA guidewire knob, which snares the knob of the STA guidewire, allowing the removal of the FA catheter snare thereby providing "through and through" access using the single wire as a platform for steering subsequent procedure equipment to a desired location.

In one embodiment of the invention, the STA guidewire is introduced into a tortuous surface vessel such as the superficial temporal artery (STA) and guided using a multi-plane imaging system which provides transverse views of the tortuous region of the STA, the transverse view perpendicular to the local axis of the tortuous vessel, and this image is used to initially guide the snare wire through the tortuous region of the STA. Once beyond this initial tortuous extent, the STA guidewire is guided using conventional radiographic imaging through the external carotid artery, then common carotid artery and from there into the aortic arch region, where it engages with the distal snare of the FA catheter. Subsequently, the FA catheter is withdrawn leaving only the STA guidewire from STA entry to FA exit, which is known as a "through and through" guidewire providing a scaffold for, and additional level of steering and control for any subsequently introduced sleeves or catheters.

In one embodiment of the invention, the through and through guidewire is used as a scaffold for a variety of different interventional procedures, including the placement of a guiding sleeve over the through and through guidewire, which can be used to subsequently guide a balloon catheter and a stent, for example, to perform angioplasty and stent installation in an affected region just beyond the end of the sleeve, which may be placed in the distal common carotid artery. The stent may be an expandable mesh, which is expanded during angioplasty to increase the diameter of the vessel and secure the stent to the vessel wall.

In another embodiment of the invention, the multi-plane imaging system is a two plane sector scanner or linear array scanner which acquires ultrasound echo information in a first set of planes which are parallel to a first axis of the transducer, and also acquires ultrasound echo information in a second set of planes which are parallel to a second axis of the transducer perpendicular to the first axis, images constructed from at least one of the first set of planes used to form a transverse image, images constructed from at least one of the second set of planes used to form a saggital image, and a coronal image formed by synthesizing echo information from the first set of planes and second set of planes using echoes received in an interval of time corresponding to a substantially uniform distance from the face of the transducer.

In another embodiment of the invention, the multi-plane imaging system is an ultrasound scanner having a plurality of imaging transducers which provide views of intersecting planes, a first plane being a transverse plane which is perpendicular to the local axis of the STA vessel, a second plane being a quasi-coronal plane which is perpendicular to the transverse plane.

A primary advantage of the present apparatus and method is improvement of navigation and placement of the carotid stent, which results in less procedure time, improved patient safety, and reduced procedural risk.

BRIEF DESCRIPTION OF THE DRAWINGS

FIG. 2A is a detail view of the aortic arch region of FIG. 1 but with a type IIB variant of the aortic arch.

FIG. 6 shows an image display reconstructed from the acquisition data organized in FIG. 4.

FIG. 7 shows an STA guidewire.

FIG. 7A shows a guidewire tip detail for FIG. 7.

FIG. 7B shows a distal end knob detail for FIG. 7.

FIG. 8 shows an FA catheter including guidewire.

FIG. 8A shows a distal tip of the FA catheter of FIG. 8.

DETAILED DESCRIPTION OF THE INVENTION

FIG. 2A illustrated the difficulty of gaining access to the internal carotid artery using the femoral artery and guiding through the sharp bends of a hostile aortic arch with a type II-A bovine variation.

Figure 1:
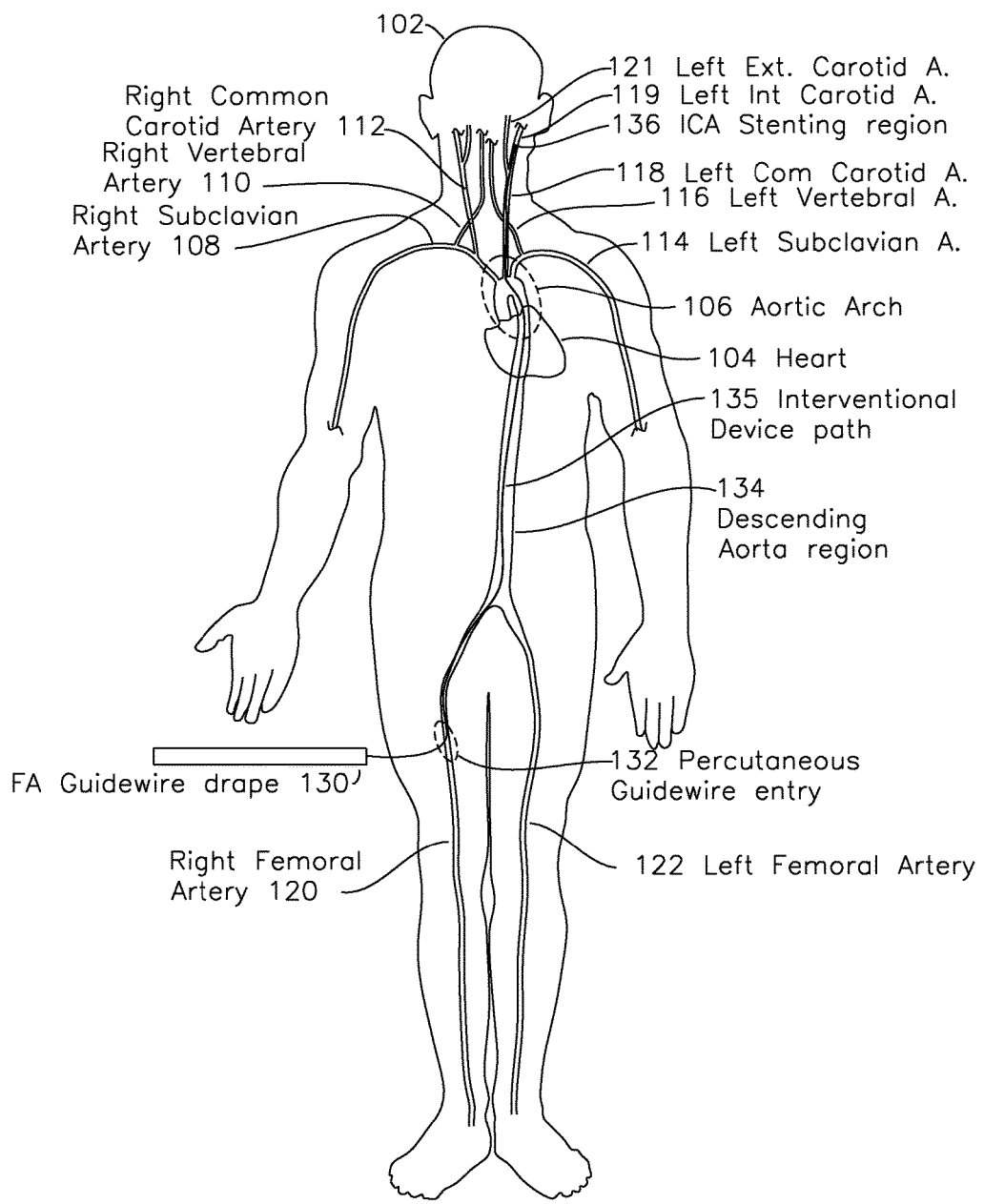
FIG. 1 is a front view of a human subject with a prior art femoral artery guidewire.
Figure 2B:
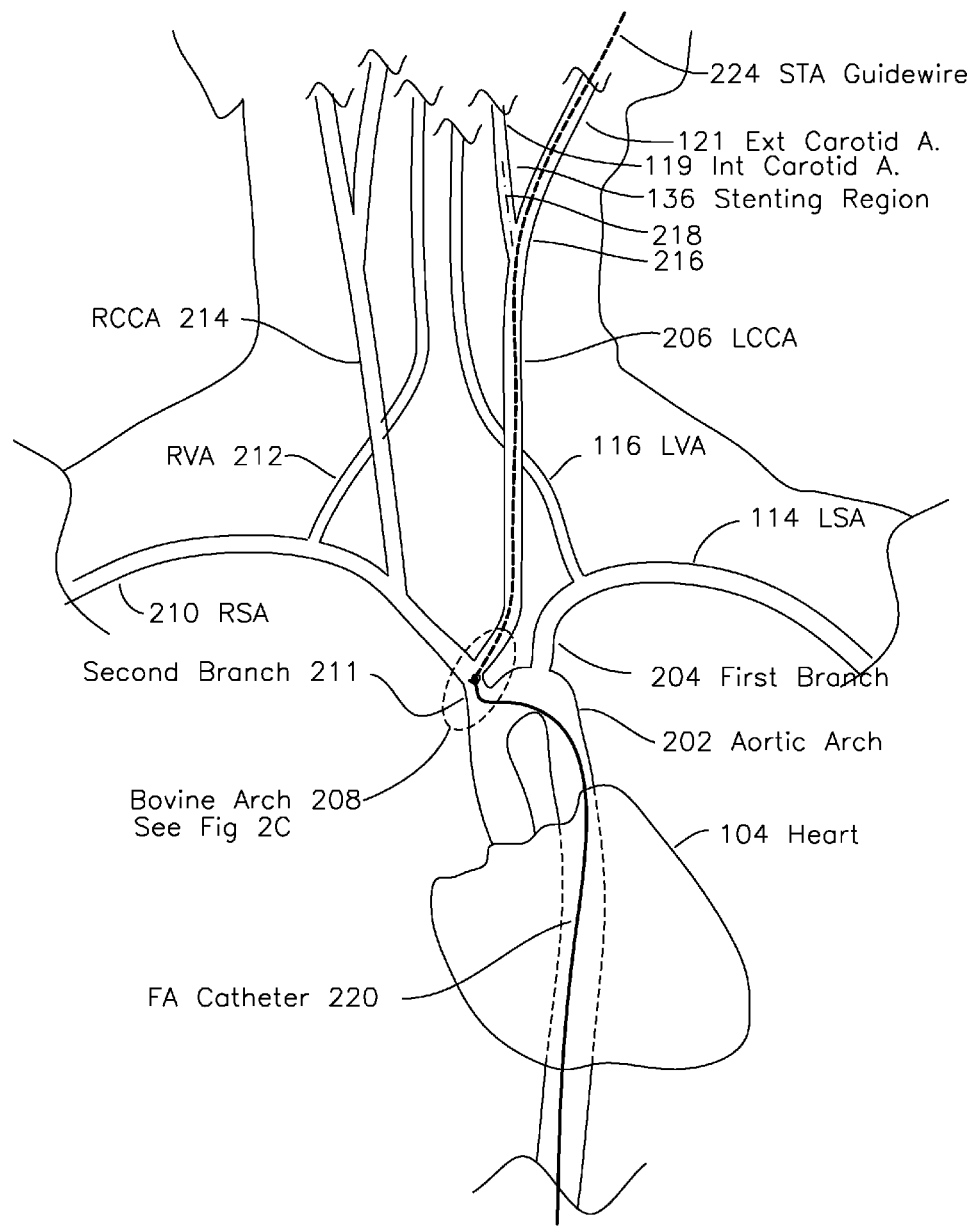
FIG. 2B is a view of FIG. 2A where an STA guidewire and FA catheter are engaged.
Figure 2C:
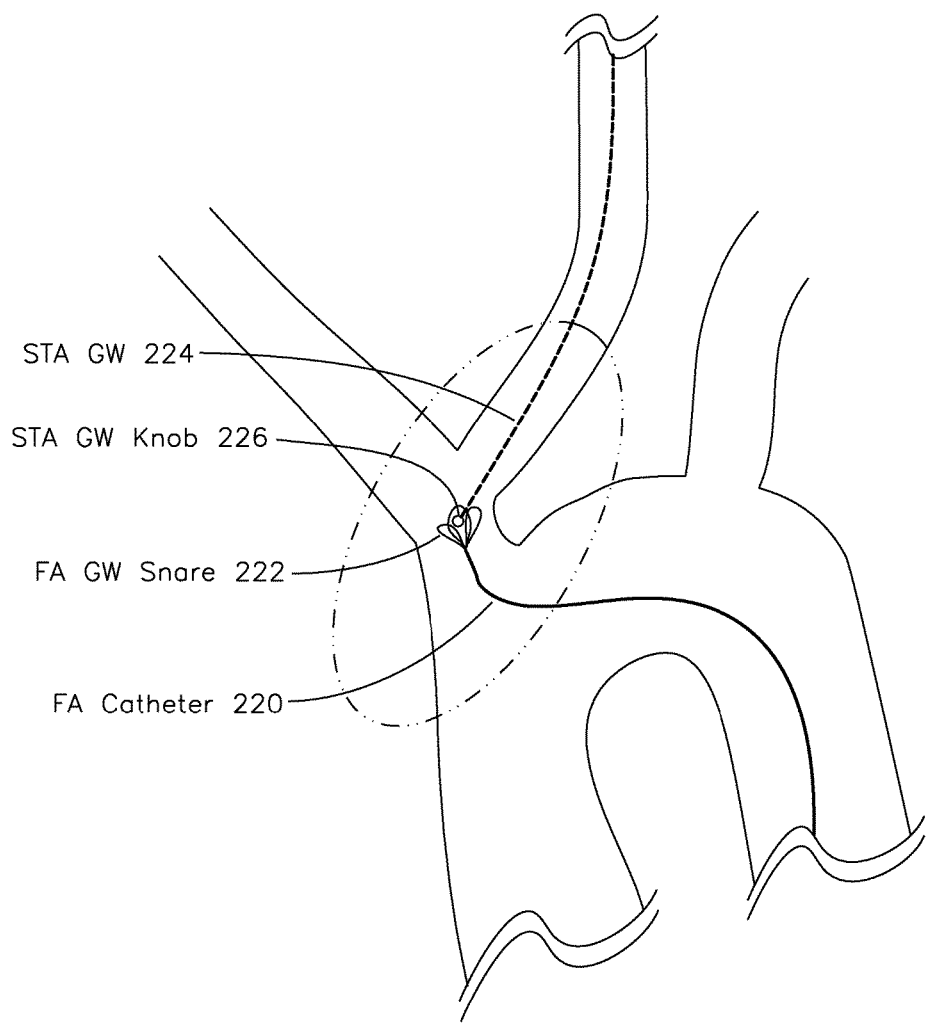
FIG. 2C is a detail view of FIG. 2B while snaring.

FIG. 2B shows a first step in gaining stenting access to the left internal carotid artery (LCA) 119 by first inserting an STA guidewire 224 with a distal head or knob which has an increased diameter near the distal end compared to the guidewire diameter, and which provides an engagement volume for the FA catheter 220 to encircle and grab, as will be described later. The STA guidewire is introduced through a needle, such as a 21 gauge needle (not shown) having an inner diameter of 0.018 inch or more, and the STA guidewire diameter may be in the range of 0.014 to 0.016 inch with the distal knob having a diameter in the range of 0.017 to 0.018 inch, and with clearance to fit within the inner diameter of the needle. Preferably, the guidewire is 0.016 inch, and the knob is 0.018 inch. The knob of the STA guidewire 224 is threaded through the STA (306 of FIG. 3), which joins the external carotid artery 121, which joins the common carotid artery 206 leading to the second branch 211 of the type II-A bovine aortic arch variation 208. The knob end of STA guidewire 224 is guided until it is in a position where it may be engaged by the FA catheter 220, and guidance and snaring is done using conventional radiographic techniques known in interventional radiology. FIG. 2C shows a magnified view of this engagement, FA catheter 220 snare end 222 encircles the knob 226 of STA guidewire 224, and the snare wires are withdrawn into FA catheter 220 to encircle and snare the STA guidewire 224 knob 226, after which the FA catheter 220 may be withdrawn from the femoral artery, thereby providing a single guidewire 224 with "through and through" access from the STA clear to the femoral artery. The STA guidewire 224 may subsequently be used as a scaffold to guide a sheath up to the bifurcation point 216 (of FIG. 2B) of the external and internal carotid artery, after which a stent guidewire may be guided along path 218 (of FIG. 2B) to the internal carotid artery 119 stent region.

Figure 2D:
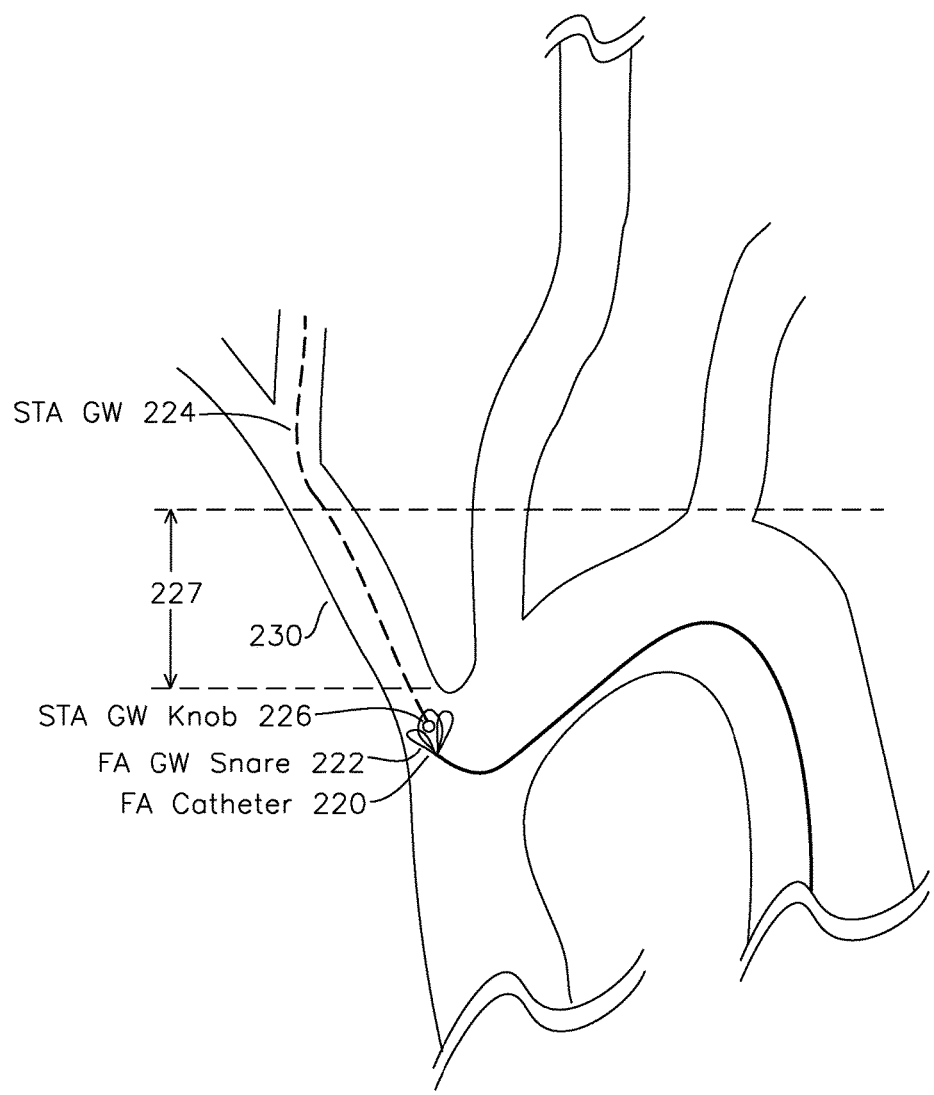
FIG. 2D is a detail view of the aortic arch region of FIG. 1 but with a type III variant of the aortic arch.

FIG. 2D shows a hostile type III aortic arch as determined by retrograde distance 227, where the FA catheter 220 which would otherwise require difficult guidance to enter vessel 230 is guided to the vessel 230 entrance and snares STA guidewire 224 after passage through vessel 230, after which FA catheter 220 is withdrawn and pulling STA guidewire 224 along with it, thereby providing through and through access using remaining STA guidewire 224 to guide subsequent interventional devices into carotid artery accessible through vessel 230, thereby greatly simplifying the guidance of interventional devices into vessel 230.

Figure 3:
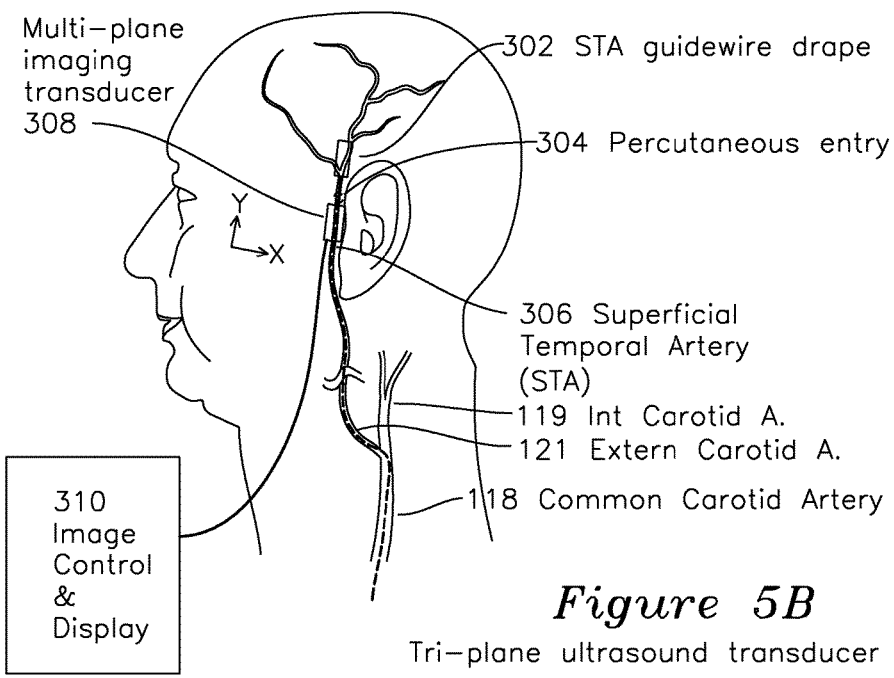
FIG. 3 is a saggital view of the STA access and ultrasound imaging transducer.

FIG. 3 shows the STA guidewire dispenser 302, which may be a surgical drape containing the unused guidewire, and percutaneous entry 304 to the STA 306. A key problem in entering and guiding the guidewire into the STA is the fragility of the STA, as well as the STA size and tortuosity. Attempting to access the STA with a needle is difficult because of the tortuosity of the artery and small size of the STA guidewire. The guidewire needle may puncture clear through the STA, and the guidewire may puncture the artery if not correctly guided. The first few centimeters of guiding are critical to the success of the STA guidewire entry, and the initial guidance requires the knowledge of the local axis position of the STA, preferably in all three planes so that the needle entry may occur parallel to this local axis (at the point of needle entry during that initial part of the procedure) and that after entry of the guidewire, that the guidewire tip may be guided substantially parallel to the local vessel axis, where the local vessel axis is understood to be taken at the distal point of the guidewire, since the underlying problem is the vessel being navigated is tortuous and the local axis is specific to a particular point.

Visualizing the STA and relationship of the needle and guidewire in the STA is provided by multi-plane ultrasound probe 308 and image processor 310, where the imaging may be accomplished by using appropriate beam focusing to provide maximum resolution near the surface of the skin where the guidewire enters the STA, and the depth of focus may be dynamically changed by the image control 310 providing electronic focus to the array elements of transducer 308, thereby maintaining sharpest focus in the region of interest.

Figure 3A:
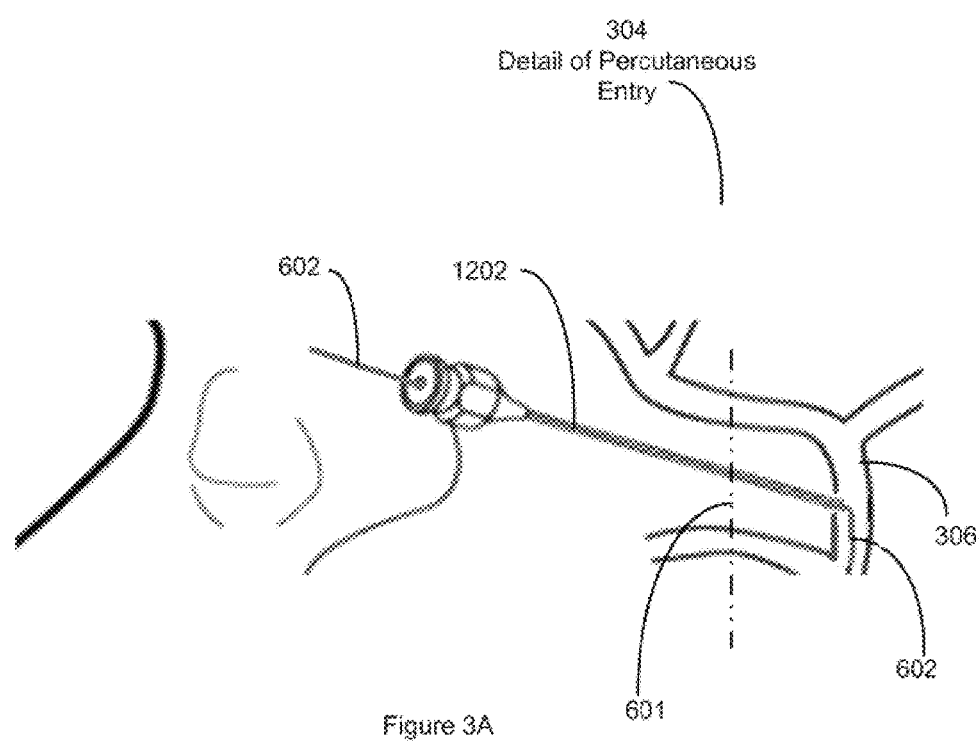
FIG. 3A is a schematic view showing the guidewire insertion needle.

FIG. 3A shows a detail of the percutaneous entry region 304 in which the needle 1202 in inserted into the STA 306. As shown in FIG. 3A, the STA guidewire 602 is inserted through an opening in the needle 1202.

Figure 4:
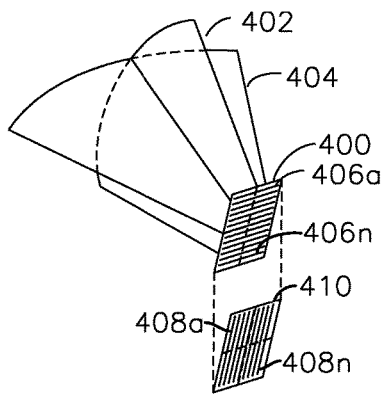
FIG. 4 is a perspective view of the imaging planes of the ultrasound transducer of FIG. 3.

FIG. 4 shows the principles of operation of an ultrasound scanner. In a 2D phased array or linear array scanner, an imaging transducer 400 is formed from plurality of rectangular elements 406a through 406n, which are each processed through a temporal variable delay line on transmit and receive, thereby providing an image plane 402 which is formed from a sequence of individual line scans, each line formed by the intrinsic transducer elements 406a through 406n focus characteristics, and a selection of transmit and receive delays provided for beam steering for off-center angular sweep shown in the extents of 402, with the individual scan lines are placed together in a 2D memory array (not shown) to form an image plane such as 402. A second plurality of rectangular elements 408a through 408n is similarly energized in transducer 410 coincident with transducer 406 on transmit and receive to form a plurality of scan lines which analogously form scan plane 404. Transducers 408 and 410 are placed adjacent to each other so that each may form the scan planes 404 and 402, respectively. In this manner, it is possible to form a 2D biplane image which is formed from the image acquisition points of plane 402 and 404. Without rotating the transducer 400, the field of view is typically limited to the two image planes 402 and 404, and inclusion of regions outside these planes is accomplished by manually rotating the angle of transducer 400 about its long or short axis. The control of transducers 400 and 410 may be provided as a linear array (a subgroup of transducer elements are energized and signals received from a superset or subset of these elements to form the image), or as a phased array (with each element receiving an appropriate phase delay to provide beam steering in the scan plane to form the image), as is known in the art of ultrasound array imaging.

Figure 5B:
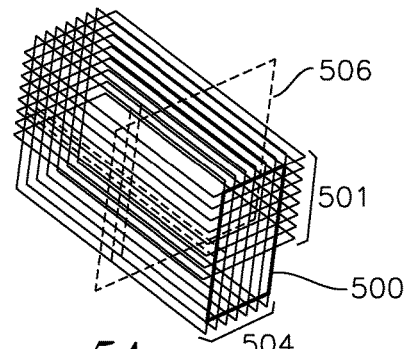
FIGS. 5A and 5B shows tri-plane acquisition of echo information from the transducer of FIG. 4.
Figure 5A:
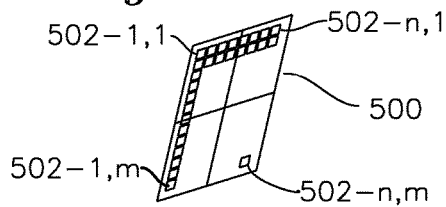

FIG. 5A shows a variant 500 of the transducer 400 shown in FIG. 4, and provides for forming the corresponding elements 406a through 406n and 408a through 408n using a two dimensional array of individual elements along one axis, shown as 502-1,1 to 502-n,1 and elements arranged on the perpendicular axis shown as 501-1,1 through 502-1,m, thereby forming an m×n array of elements, each of which is able to transmit and receive using a programmed delay. In this manner, replacing the linear arrays 404 and 410 of FIG. 4 with array 500 of FIG. 5, individual delays may be generated to cause image plane 404 to be steered up and down (not shown) as well as from side to side as shown, and image plane 402 may be steered from side to side (not shown) as well as up and down as shown, thereby forming a 3D array of acquired data, using either all vertical image data planes 504, or all horizontal image data planes 501. These acquisition image planes are shown as parallel planes in FIG. 5B for simplicity in understanding the invention, although it is known in the art of scan conversion that these may be polar arrays of image data which are converted to rectangular arrays using methods known in the art of ultrasound imaging and scan conversion. As is known in the art of ultrasound imaging, for a phased array scanner, the image planes would typically be azimuthally separated from each other by an included angle about a common axis, and for a linear array scanner, the image planes would be formed by groups of elements, forming substantially parallel planes as shown in FIG. 5B. For simplicity, the image planes indicating separately acquired images are shown in FIG. 5 as parallel planes. In one embodiment of the invention, primary image data is acquired for each of the sets of planes 501 and 504, and a third image plane 506 is synthetically created by using data from either the image plane set 502 or the image plane set 504, such as by selecting data corresponding to a separation distance from the transducer 500 face. It is also known that, by quadrature baseband mixing the return echos from the transducer after beam focusing, flow velocity may be determined throughout the volume and displayed with color intensity associated with flow rate displayed along with the ultrasound image in what is known as color flow Doppler. It is also possible to establish a sampling window by selecting a particular image depth (proportional to delay from transmit time) and thereby provide pulsed doppler flow as an audible or time-domain plot or computed value, which is known as pulsed Doppler or gate-delay Doppler. In color flow Doppler, this provides for clear identification of blood vessels containing blood flow from static structures, and for pulsed Doppler provides quantatitative information about flow velocity.

FIG. 6 shows three views constructed from image plane data of FIG. 5B. For a multi-plane transducer 308 positioned directly over the STA as shown in FIG. 3, and with a transducer long axis aligned with the local axis of the STA below the transducer 308, and using the m×n array of FIG. 5A, the transverse image 620 may be may be formed using a selected one of image data planes 501, and the saggital image 622 may be formed using a selected one of the image data planes 504. Coronal image 624 may be constructed using image data from the vertical planes 504 or horizontal image planes 501 which include the desired range of depth such as points corresponding to plane 506 to generate coronal image display 624. Accordingly, the transverse display 620 show skin surface 601, STA 604, STA guidewire 602, and cranium 606, and may be labeled with posterior and anterior views for orientation. Saggital image 622 shows skin surface 601, STA 604, guidewire 602, and cranium 606. Coronal image 624 shows the tortuous meandering of the STA 604 and guidewire 602. The combination of images 620, 622, and 624 thereby provides the information needed by an interventional radiologist to guide the STA guidewire 602 through the tortuous regions of the STA required for navigation to the common carotid artery as described previously. In one embodiment of the invention, color flow imaging or pulsed doppler flow information is provided within the images 620, 622, or 624 to further highlight the extent of vessel 604 or establish flow rates in the vessel, which may be used for guidance of the needle into the vessel, or for guidance of the guidewire through the vessel. In this view, the interior regions of STA 604 would indicate instantaneous flow, which would be useful for identifying the STA and its viability for use based on blood flow velocity from the color doppler image in the vessel or pulsed doppler information measured at the depth of the vessel from the displayed image.

FIG. 7 shows additional details of the STA guidewire 700. FIG. 7A shows the formed guidewire shape of the distal tip of the STA, which includes a 3 mm extent at the tip which is bent at an angle which is preferably substantially 24° as shown, but may be within the range from 15° to 45°. STA guidewire 704 terminates in knob 702, shown in magnified detail FIG. 7B. The STA guidewire 704 preferably has a diameter of substantially 0.014 inch, although may be within the range 0.014 inch to 0.016 inch, and knob 702 has a diameter of within the range of 0.017 to 0.018 inch, but preferably has a diameter of substantially 0.017 inch to fit within the inner diameter of a 21 gauge needle for entry into the STA through the needle. In one embodiment of the invention, multiple guidewire bends are present, including for example a first bend at the distal tip with a bend angle from 10 to 45 degrees and a second bend in the range 10 to 45 degrees separated from the first bend by 1-10 mm and placed on the opposite side from the knob end. The first and second bends may be substantially 20 degrees and the two bends separated from each other by less than 10 mm.

FIG. 8 shows an example FA catheter with a snare inserted, which as previously described and shown in magnified detail FIG. 8A, comprises outer catheter 804 and inner guidewire 802 with snare 806. The FA catheter structures are preferably in the range of 4 French to 8 French sheath enclosing an FA guidewire in the range of 0.018 to 0.038 inch in a lumen formed into the sheath which exceeds the guidewire diameter. The snare may be formed from one or more wires which form one or more loops 806 with a diameter range of 15-45 mm which may be used for snaring the STA guidewire in the aortic arch, or having a loop diameter in the range of 4 mm-8 mm for snaring the STA guidewire in the external carotid artery.

Figure 9:
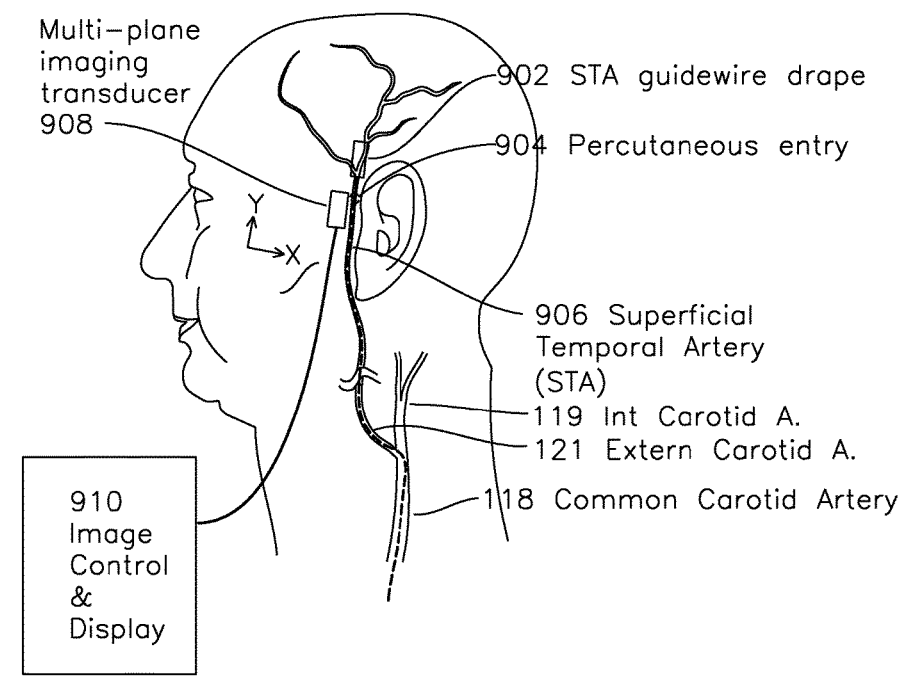
FIG. 9 shows a side-looking multi-plane imaging transducer applied adjacent to the STA of a subject.

In another embodiment of the invention shown in FIG. 9, a multi-plane ultrasound imaging probe 908 is coupled to an ultrasound imaging controller and display 910. The ultrasound probe 908 has special characteristics and performance related to imaging the STA 906 and allowing the insertion of a needle into the STA during imaging. The embodiment of FIG. 9 provides for a simpler biplane imaging system than the 3D imaging system previously described for FIG. 3, and also provides for an angular offset which provides two planes of image viewing, a transverse plane as before, and a quasi-coronal plane view which captures the tortuosity of the meandering of the STA in the coronal plane using a primary imaging plane, rather than constructing the coronal image from synthesized image data from primary 2D imaging planes as was described for FIG. 5B.

Figure 10:
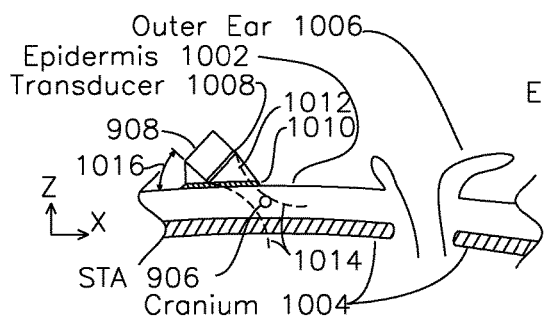
FIG. 10 shows a transverse plane view of FIG. 9.

FIG. 10 shows a transverse plane view of a subject with relationship to imaging probe 908. For the purposes of the current invention, and in accordance with how a clinician typically would use the device, the "transverse view" is a view which provides a cross section of the STA through its local axis. Accordingly, maintaining the "transverse view" as the clinician follows the progress of the guidewire in the STA may require rotating the probe 908 in a plane parallel to the epidermis 1002 (in the X-Y plane, local to the skin surface 1002). The ultrasound probe 908 includes transducer 1008 which has the characteristic of imaging in two substantially orthogonal planes as described in FIG. 4, and includes an angular offset to provide for imaging to the side of the transducer to allow simultaneous needle access at the percutaneous entry 904 and imaging access with probe 908. In one embodiment of the invention, transducer face 1008 combines two perpendicular arrays of elements which operate at different intervals of time to provide the required two planes of imaging, and the probe includes an interface which is angled to the skin surface 1002. The angle between a line normal to the face of the transducer 1008 to the local X-Y plane may be in the range of 30 degrees to 90 degrees. A basic physical tradeoff is between imaging access to the STA and needle access to the STA. As shown in FIG. 10, the region above the STA is exposed during imaging with an example angle of 45 degrees, although other angles between the transducer and skin surface 1002 are possible. A coupling gel 1010 may be provided for minimizing acoustic discontinuities between probe transducer 1008 and skin surface 1002, and angled offset coupler 1012 may be fabricated from a flexible material which provides minimal internal reflection or includes a gradient in refractive index to provides acoustic beam focusing to provide minimal beam width at the depth of the STA 906. The transducer 908 configuration of FIG. 10 thereby provides simultaneous access to the STA 906 in the region above for entry and imaging of the STA guidewire, as well as an image transverse to the local axis of the STA, shown in the X-Z plane of FIG. 10. Ear 1006 and cranium 1004 are shown for reference. Lines 1014 indicate the trend of general focus characteristics of the ultrasound beam waist in the range of the vessel, although the actual beam characteristic which provides fundamental spatial resolution is governed by the diameter of the STA being imaged, and may be adjusted by the image control 910.

Figure 11:
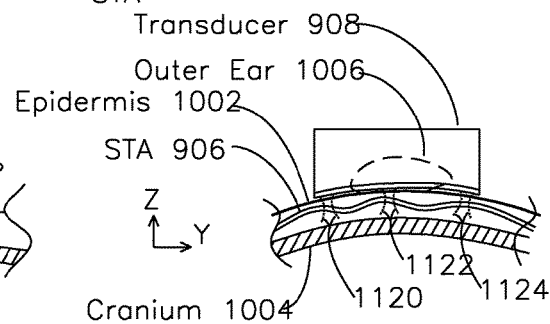
FIG. 11 shows a quasi-coronal image plane view of FIG. 9.

FIG. 11 shows a quasi-coronal plane view, where the quasi-coronal plane is orthogonal to the transverse plane of FIG. 4 and with an angle of 30 to 90 degrees, preferably 45 degrees, to the skin 1002, and shown as the Y-Z plane. The transducer 908 has a rectangular aspect ratio, which provides linear array imaging by actuating groups of individual transducers forming 908 as described in FIG. 4, thereby allowing a quasi-coronal quasi-saggital image of STA 306. An decreased angle 1016 less than 45 degrees is preferred for viewing the tortuosity (meandering) of the STA and associated guiding of the STA guidewire, since the STA meanders coronally in the tissues adjacent to the cranium, and a small angle 1016 provides for a best direct coronal view of this tortuosity. Beam profiles 1130, 1122, and 1124 indicate the progression of elements such as for a linear array, where groups of elements are energized in succession to form the rectangular array of data used to form the beam. Transducer face 908 is shown as a curved array to match the curvature of the cranium 1004, however the transducer face may be planar, or any shape which provides suitable acoustic coupling to the STA for imaging.

Figure 12:
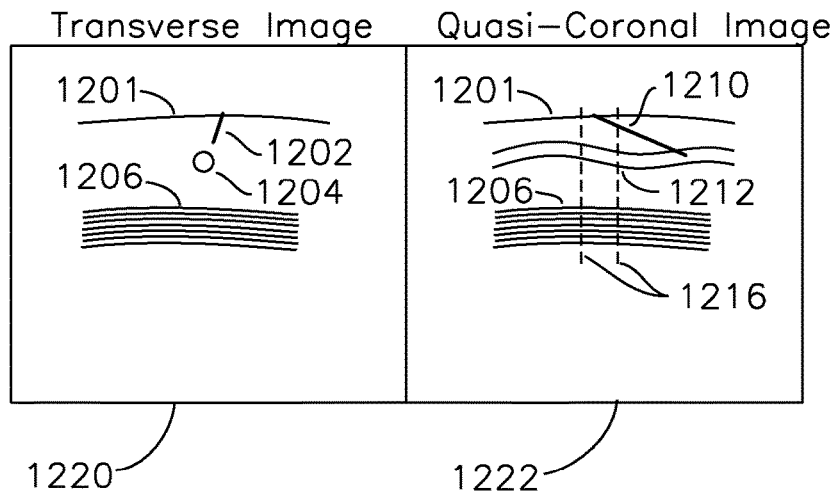
FIG. 12 shows images of a guided needle entry for FIG. 9.

FIG. 12 shows an example image display for the STA guidewire intervention of FIGS. 9, 10, and 11. The image pair 1220, 1222 of FIG. 12 indicates a simultaneous transverse image 1220 and quasi-coronal image 1222, representing the views afforded by the transducer geometry shown in FIGS. 10 and 11. The example transverse image 1220 displays ultrasound echoes indicating skin layer 1201, highly reflective cranium 1206, STA vessel 1204, and needle 1202. View 1220 would appear to show that needle 1202 has not contacted STA vessel 1204, and this example illustrates the importance of the present multi-plane scan invention, as in quasi-coronal view 1222 which is simultaneously presented, it is clear that the needle 1210 has already punctured the STA 1212 vessel first wall, but is simply out of the range of transverse focus shown by cursor lines 1216.

Figure 13:
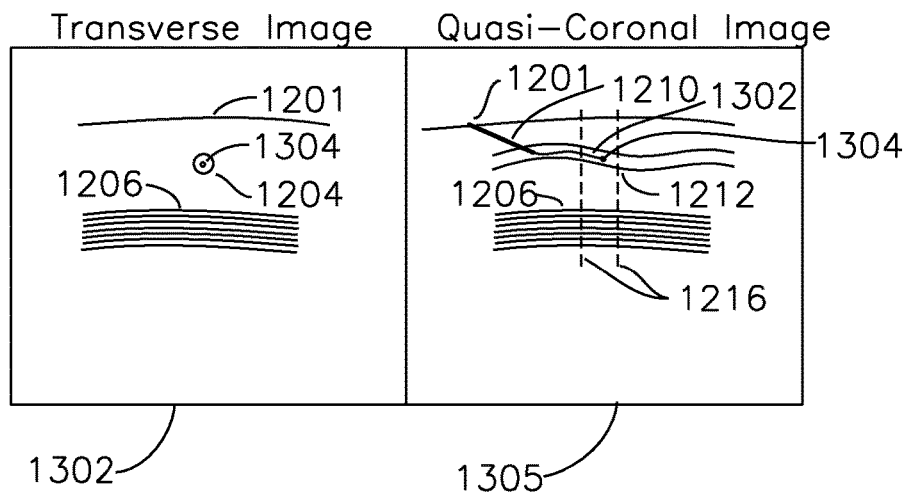
FIG. 13 shows images of a guidewire in a vessel for FIG. 12.

FIG. 13 indicates an example image display where the STA guidewire 1304 is introduced following proper location of the guidewire needle in FIG. 12 into STA 1204. The image probe is moved to along the path of the STA, so the transverse needle image is no longer visible in the image 1302 field of view, but may be seen 1210 in the quasi-coronal image 1304. Quasi-coronal image 1304 shows a view of the introduced STA guidewire 1302 and STA guidewire knob 1304, which also appears in the transverse image 1302, as it is within the transverse focus extents 1216 shown in quasi-coronal image 1305.

In another embodiment of the invention, the knob 702 of FIG. 7B may be treated with an axial winding of wire and generate a magnetic field, which magnetic field may be used in combination with the imaging techniques described herein to provide guidance of the STA guidewire within the STA using positional information provided by the magnetic field information.

In one embodiment of the invention, a multiplane reference view is provided with the multiple planes intersecting at a reference point which is aligned to guidewire tip 1304 of FIG. 13 (or needle 1202 tip of FIG. 12) such that image 1302 is selected to include this reference point, thereby showing the knob tip of the STA guidewire (or tip of the needle navigating to the tortuous artery) with visual extents 1216 provided to ensure the views are adjusted to follow the guidewire knob 1304 or needle 1202 tip. In one embodiment of the invention, this tracking is provided by an electromagnetic winding provided on the axis of the needle and guidewire in combination a proximal magnetic field detector which resolves rotation and translation of the needle or guidewire.

Because of the small size of the STA, a high frequency ultrasound transducer is preferred. It is known that the axial response of an individual scan line is associated with the temporal response of a single imaging element, and that acoustic energy propagates through the body at a rate of approximately 1.5 mm per microsecond. A typical ultrasound reflection represents 3-5 cycles at the center frequency of the transducer, and accordingly, a 10 Mhz piezoelectric transducer crystal has a temporal response of 500 us, corresponding to 0.5 mm of resolution, which is on the lower end of required resolution of the 3-4 mm STA. Accordingly, a transducer with a frequency greater than 10 Mhz is preferred, with the imaging depth limited by the Rayleigh scattering attenuation on the order of 1 db/cm/Mhz, corresponding to a 60 db SNR (relative to transmit power) imaging depth of 60 mm at 10 Mhz, or 20 mm at 30 Mhz. Accordingly, ultrasound transducer frequency ranges from 10 to 30 Mhz are expected to be preferable to provide adequate resolution as the low frequency limit and adequate penetration at the high frequency limit.

In one embodiment of the invention related to the process for placement of a stent, the STA guidewire is guided through the STA using the bi-plane ultrasound imager, the FA catheter with a bent-tip guidewire installed is introduced into the femoral artery and guided to the aortic arch region where it can snare the knob end of the STA guidewire. The locating and snaring of the knob end of the STA guidewire is done using fluoroscopic imaging, as is known in the art. The guidewire is withdrawn from the FA catheter and replaced by a snare, which is advanced through the FA catheter into the aortic arch region where it snares the knob end of the STA catheter. The STA guidewire is pulled using the snare into the FA catheter which is then pulled out through the common femoral artery access, thereby providing "through and through" access. A long guiding sleeve or sheath is then advanced over the STA guidewire into the distal common carotid artery. A second wire is now used and subsequently guided through the internal carotid artery stenosis (narrowing) until it reaches a desired region for placement of the embolic protection device. The stent is advanced over this second guidewire. The stent is expanded over the wire below the embolic protection device at the site of carotid stenosis. The embolic protection device is removed followed by removal of the second guidewire. The knob guidewire may be removed at the very end of the procedure.

In another embodiment of the invention, the STA guidewire is snared in the ECA or the CCA by initially guiding the FA catheter to the ECA or CCA, respectively.

In another embodiment of the invention, the apparatus and method may be applied to the lower extremities. For example, in a subject with a blockage in the legs such as in the tibial or pedal artery (such as diabetics) or subjects with advanced infrapopliteal occlusions, it is possible to use the multi-plane imager to guide a fine steerable guidewire through the tortuous vessels in the feet and slightly distal to the occlusion site, then thread a 3 French or 4 French catheter over the fine steerable wire, withdraw the fine steerable wire from the sheath, and then introduce a stiff guidewire in the range of 0.014 inch to 0.018 inch through the blockage, the stiff guidewire having a knob end with a knob diameter greater than the stiff guidewire diameter, and thereafter snaring the knob using an FA catheter introduced from the femoral artery and guided distally to the stiff guidewire. The stiff guidewire is then snared or guided directly into the FA catheter (if possible), and the guidewire is withdrawn or advanced through the FA catheter, thereby providing through and through access as a platform for subsequent procedures.

In another embodiment of the invention, the STA guidewire is introduced as before, however the FA catheter procedure is slightly different. In this embodiment, a sheath and first guidewire are introduced together into the femoral artery to the aortic arch region, the guidewire guiding the sheath to the desired location of the aortic arch, after which the FA catheter sleeve alone is threaded over the guidewire to the snaring location, after which the guidewire is removed and replaced with the snare such as FIG. 8A which is used to capture the knob of the STA guidewire as described earlier.

We claim:

1. A system for treatment of strokes due to arteriosclerosis in the carotid arteries, the system comprising:
   a Superficial Temporal Artery (STA) guidewire comprising a distal end, the distal end formed into a knob and having a bend for steering through rotation of the STA guidewire;
   a Femoral Artery (FA) catheter comprising a catheter body and a guidewire, the guidewire comprising a distal end having a snare for mechanical engagement with said knob, the FA catheter withdrawable from the FA with the STA guidewire to provide through and through access to the femoral artery using the STA guidewire;
   a STA guidewire insertion needle comprising an opening through which the STA guidewire is insertable;
   carotid artery arteriosclerosis interventional device comprising an opening, wherein the carotid artery arteriosclerosis interventional device is deliverable over the STA guidewire through the opening following withdrawal of the FA catheter;
   a multi-plane imaging transducer comprising a plurality of individual transducers, the multi-plane imaging transducer enabled for generating a transverse, a sagittal and a coronal image of a region including a superficial temporal artery (STA) using ultrasonic imaging techniques, by individually steering the plurality of transducers of the multi-plane imaging transducer to generate image data of at least a transverse plane, at least sagittal plane and at least a coronal plane; and
   an image control and display processor coupled to said multi-plane imaging transducer, the image control and display processor displaying a transverse view, a sagittal view, and a coronal view of the region derived from said transverse plane, sagittal plane and coronal plane image data, wherein the STA guidewire insertion needle is configured to percutaneously penetrate and enter the STA to enable insertion of the STA guidewire through the opening in the STA guidewire insertion needle into the STA, and wherein the STA guidewire, once in the STA, is configured to be guided through the STA tortuosity using the transverse, sagittal and coronal images that provide a relative distance information of the STA, the needle and the STA guidewire within the region to enable an insertion of the STA guidewire and a guidance of the STA guidewire by use of the bend in the STA guidewire, without inadvertently puncturing and creating unwanted trauma to the STA by the needle or the STA guidewire;
   wherein the STA guide wire is further configured to be steered, using the bend in the STA guidewire, to the aortic arch from the STA via the external carotid artery (ECA) and the common carotid artery (CCA).

2. The system of claim 1 wherein said STA guidewire has a diameter in the range of 0.014 inch to 0.016 inch.

3. The system of claim 1 wherein said STA guidewire knob has a diameter in the range of 0.017 inch to 0.018 inch.

4. The system of claim 1 wherein said STA guidewire has a diameter of 0.016 inch and said distal knob has a diameter of 0.018 inch.

5. The system of claim 1 wherein a bend angle of the bend in the STA guidewire is in the range 10 degrees to 45 degrees and wherein the bend is within a distance range of 2 mm to 4 mm from the distal end of said knob.

6. The system of claim 1 wherein said guidewire of said FA catheter has a diameter in the range of 0.018 to 0.038 inches.

7. The system of claim 1 wherein said FA catheter has a diameter in the range of 4 French to 8 French.

8. The system of claim 1 wherein said multi-plane imaging transducer is formed from an m×n rectangular array of individual imaging elements.

9. The system of claim 8 wherein said multi-plane imaging transducer is formed from a first array of m elements arranged along a first axis of said transducer which is adjacent to a second array of n elements arranged along a second axis perpendicular to said first axis.

10. The system of claim 1 wherein said imaging transducer comprises a piezoelectric array of elements operating in the frequency range of 10 Mhz to 30 Mhz.

11. A system for enabling a guidewire insertion into a superficial temporal artery (STA) and enabling the inserted guidewire to traverse the tortuous STA using multi-plane imaging to prevent undesired puncture of the tortuous STA, the system comprising:
- a guidewire needle configured to be inserted percutaneously into the tortuous STA;
- a guidewire configured to be inserted through the guidewire needle into the tortuous STA and guided through the tortuous STA to a treatment location,
- a multi-plane imaging transducer operable to generate ultrasound energy comprising a plurality of individually steerable ultrasound transducers that are electronically steerable, said ultrasound energy reflecting from an imaging region containing said STA, said guidewire, and said guidewire needle, said multi-plane imaging transducer thereby generating a plurality of planes of image data from the echo responses from a transducer excitation, each said plane of image data formed from a plurality of line scans, each said line scan generated by electronic steering of the individual transducers forming said multi-plane imaging transducer, said planes including at least a transverse plane of image data, and a sagittal plane of image data, said sagittal plane of image data generated perpendicular to said transverse plane of image data, and wherein said multi-plane imaging transducer generates a plane of coronal image data from said plurality of transverse image data planes and said plurality of sagittal image data planes by presenting a plurality of echo responses in each said image plane which correspond to a separation distance in the multiple planes of the STA, guidewire and guidewire needle from said transducer; and
- an image control and display processor coupled to said multi-plane imaging transducer, the image control and display processor displaying a transverse view, a sagittal view, and a coronal view of the imaging region derived from said transverse plane, sagittal plane and coronal plane showing the relative position of the STA, the guidewire needle and the guidewire in the imaging region,
- wherein the guidewire needle is percutaneously inserted into the tortuous STA using the multiple views showing the needle with respect to the location of the STA, including the separation in a plurality of dimensions, to enable accurate entry and placement of a tip of the needle into the STA and to prevent inadvertent exit puncture of the STA using the image control and display processor coupled to the multi-plane imaging transducer,
- wherein the guidewire is inserted through the guidewire needle and steered through and traverses the tortuous STA without puncturing the STA using the image control and display processor coupled to the multi-plane imaging transducer.

12. The system of claim 1, wherein the bend is a first bend and wherein distal end of the STA guidewire further comprises a second bend.

13. The system of claim 12, wherein a bend angle of the second bend is in the range of 10 degrees to 45 degrees and wherein the second bend is separated from the first bend by 1 mm to 10 mm, and wherein a bend angle of the first bend is in the range of 10 degrees to 45 degrees and wherein the first bend is separated from the distal end of the knob by 2 mm to 4 mm.

* * * * *